(12) United States Patent
Spindler et al.

(10) Patent No.: US 10,646,324 B2
(45) Date of Patent: May 12, 2020

(54) BIFURCATED STENT GRAFT WITH HEMODYNAMIC BLOOD FLOW DIVIDING WALL

(71) Applicant: Cook Medical Technologies LLC, Bloomington, IN (US)

(72) Inventors: Ralf Spindler, Bloomington, IN (US); Georgios Hilas, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 72 days.

(21) Appl. No.: 15/818,023

(22) Filed: Nov. 20, 2017

(65) Prior Publication Data

US 2018/0214259 A1 Aug. 2, 2018

Related U.S. Application Data

(60) Provisional application No. 62/452,622, filed on Jan. 31, 2017.

(51) Int. Cl.
| | | |
|---|---|---|
| *A61F 2/82* | (2013.01) | |
| *A61F 2/07* | (2013.01) | |
| A61F 2/844 | (2013.01) | |
| A61F 2/06 | (2013.01) | |

(52) U.S. Cl.
CPC ............... *A61F 2/07* (2013.01); *A61F 2/844* (2013.01); *A61F 2002/065* (2013.01); *A61F 2002/068* (2013.01); *A61F 2002/072* (2013.01); *A61F 2210/0057* (2013.01); *A61F 2220/0075* (2013.01)

(58) Field of Classification Search
CPC ........................................ A61F 2/82
See application file for complete search history.

(56) References Cited

U.S. PATENT DOCUMENTS

| | | | |
|---|---|---|---|
| 6,039,749 | A | 3/2000 | Marin et al. |
| 6,070,589 | A | 6/2000 | Keith et al. |
| 6,296,661 | B1 | 10/2001 | Davila et al. |
| 6,517,570 | B1 | 2/2003 | Lau et al. |
| 6,695,875 | B2 | 2/2004 | Stelter et al. |
| 7,160,318 | B2 | 1/2007 | Greenberg et al. |
| 7,175,652 | B2 | 2/2007 | Cook et al. |

(Continued)

FOREIGN PATENT DOCUMENTS

| | | |
|---|---|---|
| EP | 1545393 | 6/2005 |
| WO | 2005112823 | 12/2005 |

(Continued)

OTHER PUBLICATIONS

European Patent Office, European Search Report for Application No. 17207478.3, Published Jun. 1, 2018, Munich Germany.

*Primary Examiner* — Matthew W Schall
(74) *Attorney, Agent, or Firm* — Liell & McNeil

(57) ABSTRACT

A bifurcated stent graft includes a stent graft body that defines exactly one main body opening and at least two exit openings. The stent graft body includes at least one stent attached to a graft fabric material, and includes a dividing wall that divides a combined flow path, into a first flow path and a second flow path that each terminate at one of the respective exit openings. The dividing wall includes a thickness profile that terminates at a leading edge radius that extends across a width of the combined flow path.

19 Claims, 3 Drawing Sheets

(56) References Cited

U.S. PATENT DOCUMENTS

| | | |
|---|---|---|
| 7,232,459 B2 | 6/2007 | Greenberg et al. |
| 7,335,224 B2 | 2/2008 | Ohlenschlaeger |
| 7,686,842 B2 | 3/2010 | Pavcnik et al. |
| 7,722,657 B2 | 5/2010 | Hartley |
| 7,914,572 B2 | 3/2011 | Hartley et al. |
| 2002/0042644 A1 | 4/2002 | Greenhalgh |
| 2006/0229709 A1* | 10/2006 | Morris ............... A61F 2/07 623/1.31 |
| 2007/0156229 A1 | 7/2007 | Park |
| 2008/0015672 A1 | 1/2008 | Binford |
| 2014/0031920 A1 | 1/2014 | Malek |
| 2015/0018933 A1 | 1/2015 | Yang et al. |

FOREIGN PATENT DOCUMENTS

| | | |
|---|---|---|
| WO | 2006103641 | 10/2006 |
| WO | 2010027677 | 3/2010 |

* cited by examiner

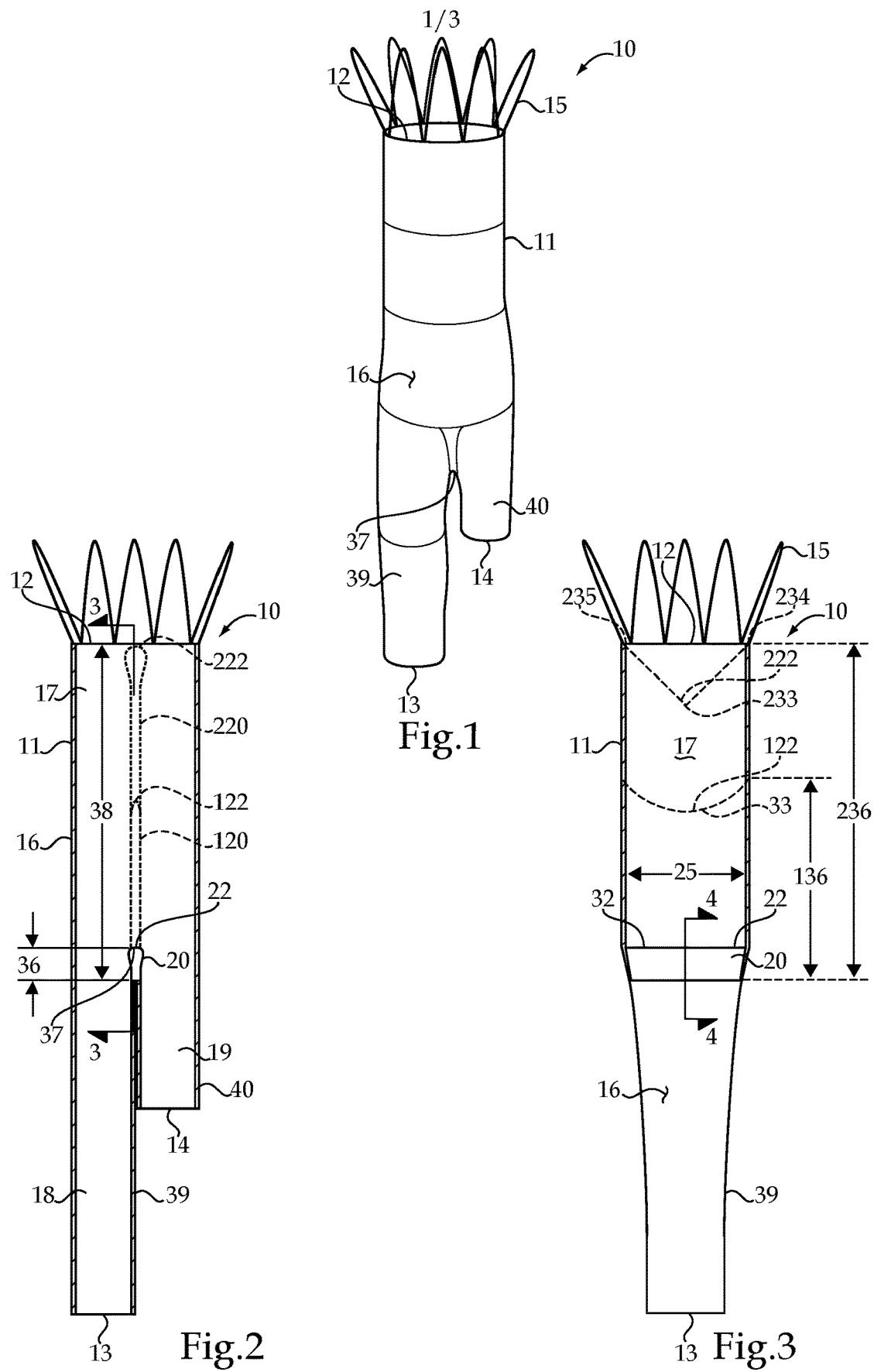

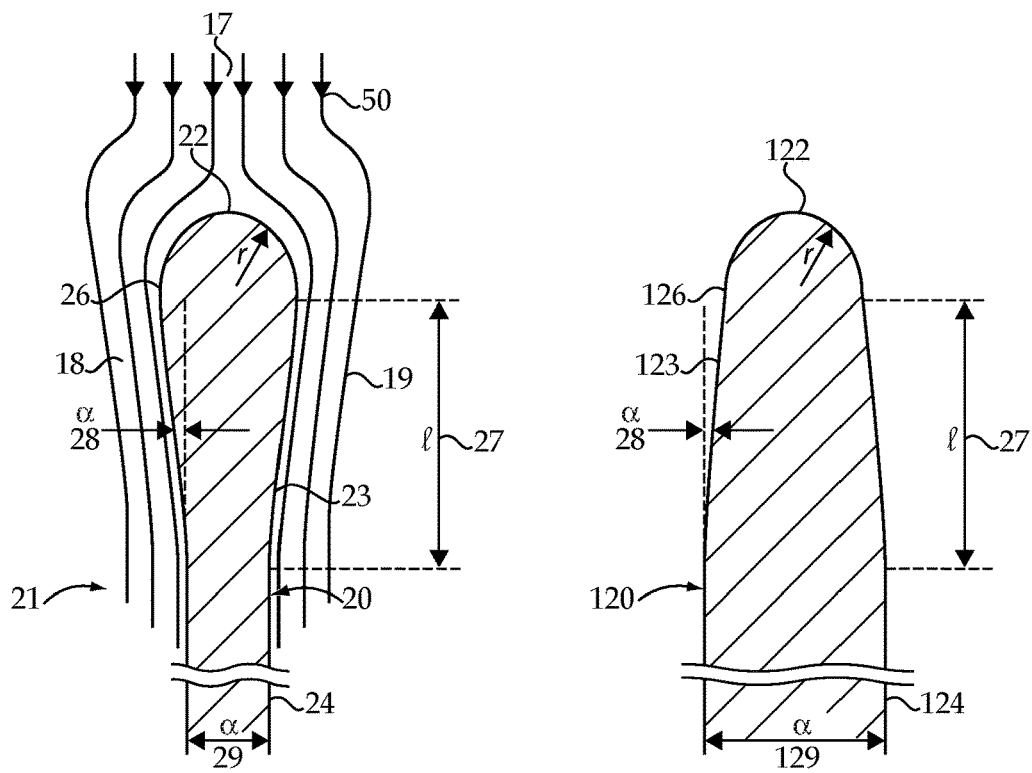
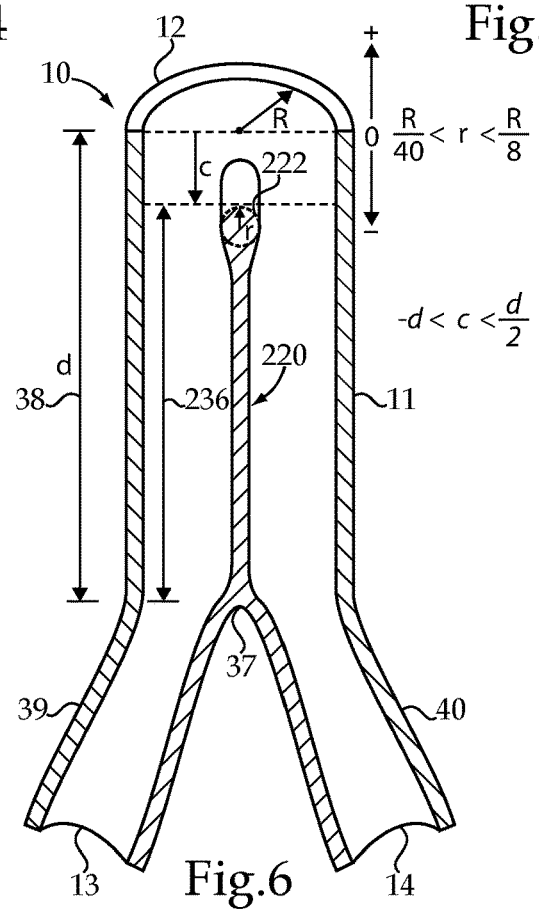

BIFURCATED STENT GRAFT WITH HEMODYNAMIC BLOOD FLOW DIVIDING WALL

TECHNICAL FIELD

The present disclosure relates generally to bifurcated stent grafts, and more particularly to a dividing wall that terminates at a leading edge radius to improve blood flow dynamics.

BACKGROUND

In some instances, abdominal aortic aneurism repair is accomplished by implanting a bifurcated stent graft that includes a combined flow path portion that spans the aneurism, and a pair of leg portions that are respectively received in the left and right iliac arteries. Although these devices have performed well for many years, researchers have observed at least one major drawback can result in an increased risk of long term complications for a patient. In particular, it is believed that blood flow dynamics, especially in the vicinity of the bifurcation of the stent graft, can cause blood cell damage and blood protein conformational changes that can lead to complications. In most applications, the bifurcation consists of a saddle area where the stent graft portions for the two iliac arteries are joined.

The present disclosure is directed toward one or more of the problems set forth above.

SUMMARY

In one aspect, the bifurcated stent graft includes a stent graft body that defines exactly one main body opening and at least two exit openings. The stent graft body includes at least one stent attached to a graft fabric material. The stent graft body includes a dividing wall that divides a combined flow path into a first flow path and a second flow path that each terminate at one of the respective exit openings. The dividing wall includes a thickness profile that terminates at a leading edge radius that extends across a width of the combined flow path.

In another aspect, a method of bifurcating flow with a bifurcated stent graft includes dividing flow from a combined flow path into a first flow path and a second flow path at a leading edge radius that is spaced from a bifurcation by a dividing wall. The flow is transitioned from the leading edge radius to a tapered segment of the wall at a tangent to the leading edge radius.

BRIEF DESCRIPTION OF THE DRAWINGS

FIG. 1 is a perspective view of a bifurcated stent graft according to the present disclosure;

FIG. 2 is a sectioned view through the bifurcated stent graft of FIG. 1;

FIG. 3 is a sectioned view through the bifurcated stent graft of FIG. 1 as viewed along section lines 3-3 of FIG. 2;

FIG. 4 is a sectioned view through a portion of a dividing wall for the bifurcated stent graft of FIGS. 1-3;

FIG. 5 is a sectioned view through a dividing wall for a bifurcated stent graft according to another embodiment of the present disclosure;

FIG. 6 is a schematic view for illustrating geometrical relationships between the dividing wall and the underlying stent graft body geometry;

DETAILED DESCRIPTION

Figure 7:
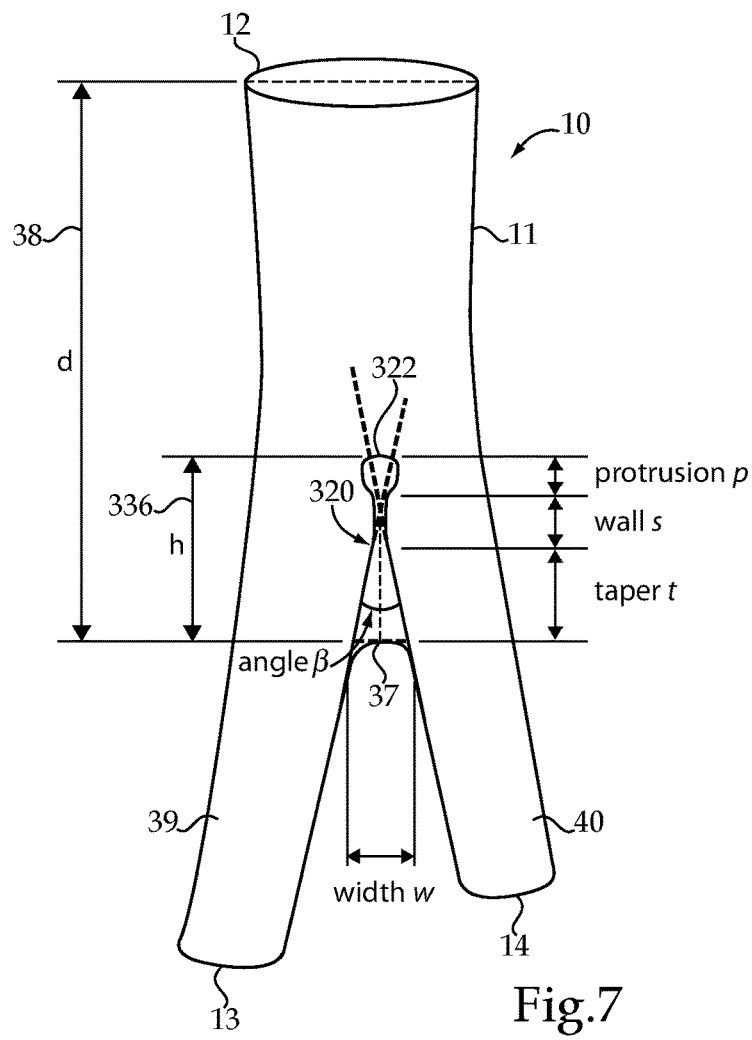
FIG. 7 is a schematic view of a bifurcated stent graft illustrating an extreme short height dividing wall aspect of the present disclosure.

Referring to all of the FIGS., a bifurcated stent graft 10, such as a stent graft utilized in abdominal aortic aneurism repair, includes a stent graft body 11 that defines exactly one main body opening 12 and at least two exit openings 13, 14. The stent graft body 11 includes at least one stent 15 attached to a graft fabric material 16. In one specific example, the stent 15 is a self expanding stent of a type well known in the art, and the graft fabric material 16 can be any suitable material known in the art. From the outside, bifurcated stent graft 10 may look much like commercially available bifurcated stent grafts that have been known and used with considerable success for years. However, a stent graft body 11 according to the present disclosure includes a dividing wall 20 (120, 220, 320, 420) that divides a combined flow path 17 into a first flow path 18 and a second flow path 19 that each terminate at one of the respective exit openings 13, 14. The dividing wall includes a thickness profile 21 that terminates at a leading edge radius 22 (122, 222, 322, 422) that extends across a width 25 of the combined flow path 17. Thus, the present disclosure teaches dividing the flow destined for the iliac arteries at the leading edge radius 22 (122, 222, 322, 422) of an internal dividing wall 20 (120, 220, 320, 420), rather than at the crotch or bifurcation 37 of the graft 10 as per the prior art.

The thickness profile 21 of the dividing wall 20 can have a variety of confirmations and still fall within the scope of the present disclosure. For instance, thickness profile 21 may include a tapered segment 23 that smoothly transitions into the leading edge radius 22 at a tangent. The tapered segment 23 may begin as a tangent 26 to the leading edge radius 22. Apart from the possible inclusion of a taper segment 23, the thickness profile 21 of the dividing wall 20 may also include a uniform thickness segment 24. In this context, "uniform thickness" means that this segment has no evident taper, but may show some variability due to the underlying materials (e.g. metallic stenting). The dividing wall 20 may be formed at least partially of the same material as the graft fabric material 16 and may stretch between opposite sides of the stent graft body 11, and may or may not include metallic stent reinforcement. The leading edge radius 22 as well as the contiguous tapered segment 23 or uniform thickness segment 24 may be also formed from the graft fabric material 16, and or may also include a formed feature, such as from plastic, to shape the thickness profile 21 in general, and the leading edge radius 22, in particular. The tapered segment 23 may have a length 27 ($l$) greater than double a radius r of the leading edge radius 22. In two specific examples, shown in FIGS. 4 and 5, respectively, a taper angle 28 ($\alpha$) of the tapered segment 23, 123 may be a function 30, 130 of the radius r of the leading edge radius 22, 122, the length 27 ($l$) of the tapered segment 23, 123 and a thickness 29, 129 ($a$) of the uniform thickness segment 24, 124. As shown in FIG. 4, the tapered segment 23 may thin toward the leading edge radius 22, or as shown in FIG. 5, the tapered segment 123 may thicken toward leading edge radius 122.

The dividing wall 20 has a height 36 that extends from the bifurcation 37 of the stent graft body 11 to the leading edge radius 22. In the solid line illustrated embodiment of FIG. 2, the height 36 is a minority of a distance 38 from the main body opening 12 to the bifurcation 37. Nevertheless, the present disclosure also contemplates a dividing wall height 136 corresponding to a leading edge radius 122 that is about half the distance 38 from the main body opening 12 to the bifurcation 37. About half means that when the ratio of the height 136 to the distance 38 is rounded to a fraction with a 1 in the numerator, then the denominator, when rounded to a single significant digit, is 2. In still another embodiment, the designer may opt to have the flow divide even closer to the main body opening 12. For instance, a dividing wall height 236 may be a majority of the distance 38 from the main body opening 12 to the bifurcation 37. A leading edge radius 222 positioned at the main body opening 12 would also be considered as dividing the combined flow path 17, and would still fall within the scope of this disclosure. The height 236 of the dividing wall 20 may be longer than the first leg 39 and the second leg 40 or, the height 36 of the dividing wall 20 may be shorter than both the first leg 39 and the second leg 40. Or, the height 136 of the dividing wall 120 may be about equal to a length of one of the legs 39 or 40. About equal means that when the two lengths are ratioed, and rounded to a single significant digit, that number is one.

The present disclosure also contemplates different leading edge shapes across a width 25 of the combined flow path 17. For instance, the solid line illustrated embodiment (FIG. 2) shows a straight line 32 across the width 25. The dashed line for the leading edge radius 122 shows that the leading edge radius 122 may be presented as a curved line 31 across the width 25, which is convex to the flow path. In still another example, the leading edge radius 222 may have a center 233 of the width 25 that is further from the main body opening 12 than the two sides 234 and 235 of the width 25. Any of these different width shapes of the leading edge radius (22, 122, 222) can go with any of the different wall heights 36, 136, 236 without departing from the present disclosure. Other leading edge width profiles, including a convex shape, would also fall within the intended scope of the present disclosure.

Although FIGS. 4 and 5 suggest that the cross sectional view of the tapered segment 23 and the leading edge radius 22 may be uniform across width 25, this need not necessarily be so, and still fall within the intended scope of the present disclosure. However, although the radius r may be different at different locations across the width 25, the blood flow will still be split at a leading edge radius 22, 122, 222 that more atraumatically and efficiently splits the flow prior to arrival at the iliac arteries. Although the present disclosure is illustrated in the context of a bifurcated stent graft in which one of the two exit openings 13 is further from the main body opening 12 than the other of the two exit openings 14, any bifurcated stent graft could fall within the scope of the present disclosure. Thus, in the illustrated embodiment the stent graft body 11 has a first leg 39 that extends from the bifurcation 37 to the exit opening 13, and a second leg 40 that extends from the bifurcation 37 to the other exit opening 14. A bifurcated stent graft according to the present disclosure need not necessarily be of the type typically associated with abdominal aortic aneurism repair.

Figure 8:
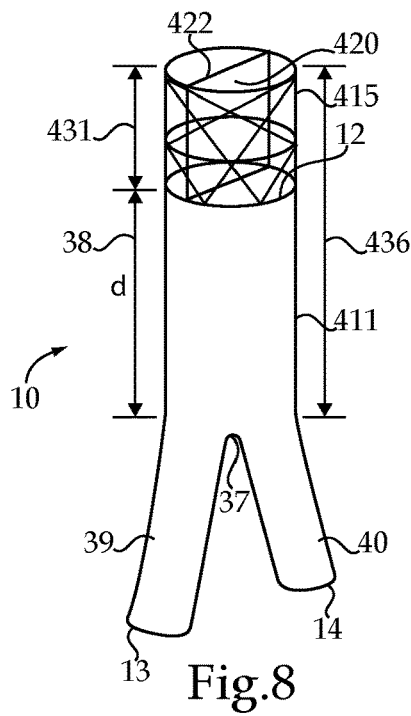
FIG. 8 is a schematic view of still another bifurcated stent graft showing an extreme tall version of the dividing wall aspect of the present disclosure.

Referring now specifically to FIG. 6, a schematic view of a bifurcated stent graft 10 is used to illustrate a range of relationships between the radius r of the dividing wall 220 to the geometry of the stent graft body 11. In particular, where R is the radius of the main body opening 12 and r is the radius of the leading edge radius 222, an equation expressing the range of the leading edge radii to the radius R of the main body opening is shown in FIG. 6. Also, FIG. 6 is useful in illustrating a relationship between the distance c between the main body opening 12 and the tip of the leading edge radius 222 in relation to the distance d from the main body opening 12 to the bifurcation 37. Thus, in one extreme (FIG. 7), the dividing wall 320 can be very short but does have some height from bifurcation 37 On the other-hand, in another extreme case as shown in FIG. 8, the dividing wall 420 may extend outside of the main stent graft body 11 and beyond or upstream from the main graft opening 12. In such an instance, the extended portion of the dividing wall 420 that extends above main body opening 12 may be supported by bare metal stent structure 415 that may be uncovered by any fabric as in the stent graft body 11. The height 431 of the dividing wall 420 that extends above main body opening 12 may be about half the distance d 38 from the main body opening 12 to the bifurcation 37 as per the equation expressed in FIG. 6. Thus, in one extreme case illustrated in FIG. 8, the overall height 436 of the dividing wall 420 may be longer than the distance d 38 from the main body opening 12 to the bifurcation 37 and still fall within the scope of the present disclosure. Referring to FIG. 7, a set of equations and dimensions are provided for illustrating an extreme short height version of a dividing wall 320 according to the present disclosure. In particular, the illustration of FIG. 7 is extremely out of scale to show the geometry but the numbers in the box to the right hand side show that the dimensions can be relatively small. In particular, the height h 336 of the dividing wall 320 is the sum of the height of the protrusion portion p that includes the leading edge radius 322, the height of wall s, which was earlier referred to as a uniform wall segment and the height of taper t. The dividing angle $\beta$ in one extreme is calculated as the arc tangent of s+t over ½ a width w of the bifurcation 37. Assuming that the bifurcation width is 0.1 millimeter, that the height of protrusion p is 0.5 millimeters and that the dividing angle $\beta$ is 10°, we arrive at a minimum height for the dividing wall 320 as being 0.1 millimeters. Thus, the present disclosure contemplates dividing walls that extend from a fraction of a millimeter above the bifurcation 37 all the way to dividing walls that are actually longer than the length d of the main body segment of the bifurcated stent graft 10.

A variety of different structures are considered for the dividing wall 20 (120, 220, 320, 420). Among these, the leading edge radius 22 (122, 222, 322, 422) could be a coated or an un-coated polymer, such as PTFE, or the leading edge radius 22 (122, 222, 322, 422) could be coated with an elastic (soft) layer to reduce cellular stress that might occur when the blood cells impact the leading edge radius 22 (122, 222, 322, 422). This soft coating may have a Young's Modulus from 1-5 MPa, or similar to endothial tissue. A lower Young's Modulus than natural tissue (e.g., 0.1 MPa) may also be desirable. Apart from being soft, the leading edge radius 22 (122, 222, 322, 422) should be smooth to increase the likelihood of laminar blood flow. The dividing wall 20 (120, 220, 320, 420) may use materials similar or commonly used as stent graft fabric material 16 including but not limited to DACRON, esPTFE with urethane, ePTFE, and others known in the art. The surface properties of the taper (if any) and the remaining portions of the dividing wall 20 (120, 220, 320, 420) may be harder than that of the leading edge radius 22 (122, 222, 322, 422). In addition, the remaining portions of dividing wall 20 (120, 220, 320, 420) may be rougher than the leading edge radius 22 (122, 222, 322, 422) for improved blood flow dynamics, possibly finding an analogy in the roughness of a shark skin surface. Overall, the surface properties may be modified by a coating procedures of additional materials such as nanomaterials and/or polymers. On the otherhand, there may be no difference leading edge, wall and taper properties. The dividing wall 20 (120, 220, 320, 420) may be attached on opposite sides to the stent graft body 11 using surgical sutures or any other strategy known in the art. The dividing wall 20 (120, 220, 320, 420) in general, and the leading edge radius 22 (122, 222, 322, 422) in particular could be strengthened with stent frame material (e.g., nitinol, CoCr, stainless steel, etc.) arranged in such a way to allow crimping of the stent graft 10 within a delivery sheath in a conventional manner.

INDUSTRIAL APPLICABILITY

The present disclosure finds potential application in any bifurcated stent graft application. The present disclosure finds more particular applicability to bifurcated stent grafts for use in the blood circulatory system. Finally the present disclosure finds specific application in bifurcated stent grafts of the type used for abdominal aortic aneurism repair.

A bifurcated stent graft 10 according to the present disclosure may be delivered to a treatment site using known delivery devices and techniques. For instance, the bifurcated stent graft 10 might be compressed about a delivery catheter and covered by a retractable sheath, which is withdrawn at the delivery site to allow the stent graft 10 to self expand to the shape shown in FIG. 1. When the stent graft 10 expands at the delivery site, the previously compressed dividing wall 20 also expands into the configuration shown, for instance, in FIGS. 2 and 3. When this occurs, flow from the combined flow path 17 upstream from or at the main body opening 12 is divided into a first flow path 18 and a second flow path 19 at leading edge radius 22, which is spaced from an bifurcation 37 by dividing wall 20. The flow may transition from the leading edge radius 22 to a tapered segment 23 of the wall 20 at a tangent to the leading edge radius 22. Thereafter, the flow may transition from the tapered segment 23 to a uniform wall segment 24 prior to reaching one of the individual legs 39 and 40 of the bifurcated stent graft 10.

By appropriately choosing the thickness profile 21 of the dividing wall 20 and the radius r of the leading edge radius 22, less sheer stress may be encountered by blood components, potentially leading to less damage to blood cells and the like due to impact at the dividing point. Furthermore, by using an appropriate surface material and shapes, less or no damage may occur to blood components after the bifurcated stent graft 10 is in place. Furthermore, by making the leading edge radius 22 (122, 222, 322, 422) soft like live tissue, less impact damage to blood cells could be expected.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A bifurcated stent graft comprising:
   a stent graft body defining exactly one main body opening and at least two exit openings;
   the stent graft body includes at least one stent attached to a graft fabric material, a bifurcation and a dividing wall that divides a combined flow path into a first flow path and a second flow path that each terminate at one of the respective exit openings; and
   the dividing wall includes a thickness profile that terminates at a leading edge radius that extends across a width of the combined flow path.

2. The bifurcated stent graft of claim 1 wherein the thickness profile of the dividing wall includes a tapered segment that begins as a tangent to the leading edge radius.

3. The bifurcated stent graft of claim 2 wherein the tapered segment has a length greater than double the leading edge radius.

4. The bifurcated stent graft of claim 3 wherein a taper angle of the tapered segment is a function of the leading edge radius and the length of the tapered segment.

5. The bifurcated stent graft of claim 2 wherein the tapered segment thins toward the leading edge radius.

6. The bifurcated stent graft of claim 2 wherein the tapered segment thickens toward the leading edge radius.

7. The bifurcated stent graft of claim 1 wherein one of the two exit openings is further from the bifurcation than an other one of the two exit openings.

8. The bifurcated stent graft of claim 1 wherein the leading edge radius is further from the bifurcation than the main body opening.

9. The bifurcated stent graft of claim 1 wherein the leading edge radius is less than one eight of a radius of the main body opening.

10. The bifurcated stent graft of claim 1 wherein the leading edge radius defines a curved line across the width.

11. The bifurcated stent graft of claim 1 wherein the leading edge radius defines a straight line across the width.

12. The bifurcated stent graft of claim 1 wherein the leading edge radius at a center of the width is further from the main body opening than each side of the width.

13. The bifurcated stent graft of claim 1 wherein the dividing wall has a height that extends from the bifurcation to the leading edge radius;
   the height is a majority of a distance from the main body opening to the bifurcation.

14. The bifurcated stent graft of claim 1 wherein the dividing wall has a height that extends from the bifurcation to the leading edge radius;
   the height is a minority of a distance from the main body opening to the bifurcation.

15. The bifurcated stent graft of claim 1 wherein the dividing wall has a height that extends from the bifurcation to the leading edge radius;
   the stent graft body has a first leg that extends from the bifurcation to one of the exit openings, and a second leg that extends from the bifurcation to an other one of the exit openings;
   the height is longer than the first leg and the second leg.

16. The bifurcated stent graft of claim 1 wherein the dividing wall has a height that extends from an bifurcation to the leading edge radius;
   the stent graft body has a first leg that extends from the bifurcation to one of the exit openings, and a second leg that extends from the bifurcation to an other one of the exit openings;
   the height is shorter than the first leg and the second leg.

17. The bifurcated stent graft of claim 1 wherein the dividing wall has a height that extends from the bifurcation to the leading edge radius;
   the stent graft body has a first leg that extends from the bifurcation to one of the exit openings, and a second leg that extends from the bifurcation to an other one of the exit openings;
   the height is about a same length as at least one of the first leg and the second leg.

18. A bifurcated stent graft comprising:
   a stent graft body defining exactly one main body opening and at least two exit openings;

the stent graft body includes at least one stent attached to a graft fabric material, a bifurcation and a dividing wall that divides a combined flow path into a first flow path and a second flow path that each terminate at one of the respective exit openings;

the dividing wall includes a thickness profile that terminates at a leading edge radius that extends across a width of the combined flow path; and wherein the dividing wall has a height that extends from a bifurcation to the leading edge radius in a direction of the main body opening.

19. A bifurcated stent graft comprising:

a stent graft body defining exactly one main body opening and at least two exit openings;

the stent graft body includes at least one stent attached to a graft fabric material, a bifurcation and a dividing wall that divides a combined flow path into a first flow path and a second flow path that each terminate at one of the respective exit openings; and the dividing wall includes a thickness profile that terminates at a leading edge radius that extends across a width of the combined flow path;

wherein flow entering the stent graft at the main body opening is split and destined for one of the two exit openings at the leading edge radius rather than at a bifurcation of the bifurcated stent graft.

* * * * *